United States Patent
Nadimi Zahedani

(10) Patent No.: US 10,806,168 B2
(45) Date of Patent: Oct. 20, 2020

(54) FOOD SUPPLEMENT, PROCESS FOR PREPARING IT AND ITS USES

(71) Applicant: Dario Nadimi Zahedani, Leghorn (IT)

(72) Inventor: Dario Nadimi Zahedani, Leghorn (IT)

(*) Notice: Subject to any disclaimer, the term of this patent is extended or adjusted under 35 U.S.C. 154(b) by 0 days.

(21) Appl. No.: 16/322,555

(22) PCT Filed: Aug. 1, 2017

(86) PCT No.: PCT/EP2017/069416
§ 371 (c)(1),
(2) Date: Feb. 1, 2019

(87) PCT Pub. No.: WO2018/024716
PCT Pub. Date: Feb. 8, 2018

(65) Prior Publication Data
US 2019/0191753 A1   Jun. 27, 2019

(30) Foreign Application Priority Data

Aug. 3, 2016 (IT) .............................. UA2016A5779

(51) Int. Cl.
| | |
|---|---|
| A61K 36/00 | (2006.01) |
| A23L 33/105 | (2016.01) |
| A61K 33/14 | (2006.01) |
| A61K 36/61 | (2006.01) |
| A61K 36/63 | (2006.01) |
| A61K 41/13 | (2020.01) |
| A23L 33/16 | (2016.01) |
| A61P 9/12 | (2006.01) |
| A61P 13/12 | (2006.01) |
| A61P 19/10 | (2006.01) |
| A61K 9/12 | (2006.01) |

(52) U.S. Cl.
CPC ............. *A23L 33/105* (2016.08); *A23L 33/16* (2016.08); *A61K 9/12* (2013.01); *A61K 33/14* (2013.01); *A61K 36/61* (2013.01); *A61K 36/63* (2013.01); *A61K 41/13* (2020.01); *A61P 9/12* (2018.01); *A61P 13/12* (2018.01); *A61P 19/10* (2018.01); *A23V 2002/00* (2013.01); *A23V 2200/15* (2013.01); *A23V 2200/316* (2013.01); *A23V 2200/326* (2013.01); *A23V 2250/21* (2013.01); *A23V 2300/48* (2013.01); *A61K 2236/00* (2013.01); *A61K 2236/50* (2013.01)

(58) Field of Classification Search
CPC ....................................................... A61K 36/00
USPC ......................................................... 424/725
See application file for complete search history.

(56) References Cited

FOREIGN PATENT DOCUMENTS

| CN | 104705627 A | 6/2015 |
|---|---|---|
| CN | 104922220 A | 9/2015 |
| CN | 104982941 A | 10/2015 |
| JP | 2011072307 A | 4/2011 |
| WO | WO2009133409 A1 | 11/2009 |

OTHER PUBLICATIONS

Khemakhem Ibtihel et al. "Kinetic improvement of olive leaves' bioactive compounds extraction by using power ultrasound in a wide temperature range", Ultrasonics, Jun. 11, 2016, Great Britain; XP029776395.

Panagiotis Efentakis et al., "Effects of the Olive Tree Leaf Constituents on Myocardial Oxidative Damage and Atherosclerosis", Planta Medica, May 27, 2015, Germany; XP055376359.

Sedef, et al., "Olive tree (*Olea europaea*) leaves: potential beneficial effects on human health", Nutrition Reviews Nov. 1, 2009; XP055136530.

Scheffler, et al., "*Olea europaea* leaf extract exerts L-type Ca channel antagonistic effects", Journal of Ethnopharmacology; 2008; Germany.

Garcia, et al., "Antioxidant activity of phenolics extracted from *Olea europaea* L. leaves", Food Chemistry; Sep. 1999.

Susalit, et al., "Olive (*Olea europaea*) leaf extract effective in patients with stage-1 hypertension: Comparison with Captopril"; Elsevier; 2010.

Perrinjaquet-Moccetti, et al., "Food Supplementation with an Olive (*Olea europaea* L.) Leaf Extract reduces blood pressure in borderline hypertensive monozygotic twins", Phytotherapy Research; 2008.

*Primary Examiner* — Michael V Meller
(74) *Attorney, Agent, or Firm* — King & Schickli, PLLC

(57) ABSTRACT

The present invention refers to a process for preparing a salt solution comprising sodium chloride and extracts of parts of officinal plants, preferably extracts of olive tree leaves; the invention is further directed to the salt solution itself, optionally enriched in iodine, particularly in a spray formulation, and to its uses as food supplement, as flavour enhancer for reducing salt consumption and for preventing cardiovascular and renal diseases, osteoporosis, and diseases related to salt abuse and/or iodine insufficiency in the diet.

12 Claims, 1 Drawing Sheet

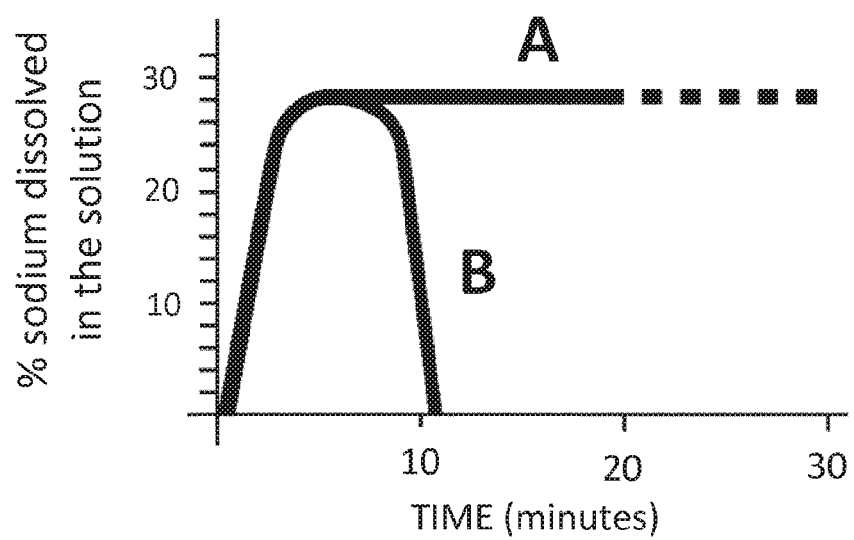

FOOD SUPPLEMENT, PROCESS FOR PREPARING IT AND ITS USES

TECHNICAL FIELD

The present invention refers to a process for preparing a salt solution comprising sodium chloride and officinal plant extracts, also from organic farming; the invention further refers to the salt solution itself—particularly in a spray formulation—and to its uses as food supplement, as flavor enhancer and for preventing or treating cardiovascular diseases and other pathologies caused by salt abuse. Preferred officinal plant extracts include extracts from olive leaves and/or extracts from Acca sellowiana fruits and leaves.

BACKGROUND OF THE INVENTION

Common salt (i.e. sodium chloride, NaCl), also generally referred to as salt or cooking salt or table salt, is an element by now popular in cooking and it is typically used for different purposes such as, for instance, to enhance flavours, to preserve the food (by inhibiting the microorganisms that spoil it), and to reach certain food consistencies.

One of the most common problems linked to this food is its abuse, a circumstance supported by recent investigations carried out by the World Health Organization (WHO).

As a matter of fact, it has been estimated that the present average consumption in adult population in Europe ranges from 8 to 12 g/day per capita, whereas WHO recommends to use no more than 5 g/day of salt per capita.

It is therefore inferred that the per capita consumption of salt is approximately 2 to 3 times greater than the recommended dietary allowance.

Abuse of this substance entails and causes the onset of different pathologies, typically hypertension, cardiovascular and renal pathologies or, with special reference to the female population, osteoporosis, water retention, and cellulite. Reducing the intake of such substance would certainly lead to benefits in terms of improved health and reduction in costs dedicated to the care of the above listed pathologies and problems.

However, renouncing the taste of salt in meals is difficult for consumers. Also, measuring the actual quantity of it that is added every day to the food, especially when eating out, is substantially impossible.

This is the reason why there is a keen interest, even by the Ministries of Health in various Countries, in finding ways to reduce the daily consumption of salt in adult population.

Further to the reduction of daily consumption of salt, the public health Ministries have interest in increasing iodine intake in the population. In fact, iodine is essential for healthy brain development in the fetus and young child and its deficiency negatively affects the health of women, as well as economic productivity and quality of life.

Most people need an additional source of iodine as it is found in relatively small amounts in the diet.

An effective strategy to increase iodine intake at the population level is iodization of salt for human consumption, that is the process of fortifying salt with iodine. The concentration of iodine in salt can be thus adjusted as needed. However, it is still essential to monitor the levels of iodine intake with salt to ensure that the population's needs are met and not exceeded. In the light of investigating further ways to decrease the pathologies bound to salt abuse, such as hypertension, renal dysfunction, osteoporosis, water retention and cellulite, as described above, a number of studies have been carried out relating to the phytotherapic effect of different plants, such as those indicated by the Italian Ministry of Health itself, International pharmacopoeia and well-established practice of traditional herbal remedies.

For instance, it is known that the most suitable plants having a phytotherapic effect for cardiovascular health include: garlic (*Allium sativum* L.), preferably its bulbs; common hawthorn (*Crataegus monogyna*), preferably its leaves; basil (*Ocimum Basilicum*), preferably its leaves; capsicum (*Capsicum annuum*), preferably its fruits; common olive (*Olea europaea* L.), preferably its leaves; pepper (*Piper nigrum* L.), preferably its fruits; rosemary (*Rosmarinus officinalis*), preferably its leaves; ginger (*Zingiber Officinalis* R.), preferably its rhizome. Preferably, the leaves of common olive are particularly recommended.

It is also known that the most indicated plants having a phytotherapic effect for water retention and renal apparatus include: birch (*Betula pendula* R.), preferably its leaves; horsetail (*Equisetum Arvense* L.), preferably its buds; green tea (*Camellia sinensis* L. K.), preferably its leaves; taraxacum (*Taraxacum officinale*), preferably its leaves and roots. It is also known that the most suitable plant having a phytotherapic effect for osteoporosis is horsetail (*Equisetum Arvense* L.), preferably its buds and herb.

It is also known that the most suitable plant having a high natural content of iodine is Feijoa selloviana (Acca sellowiana (O. Berg) Burret), preferably its fruits and leaves.

In particular, it has been widely demonstrated that the olive leaves extract (OLE) comprises compounds that have a strong hypotensive action (amongst other, see for instance Scheffler A. et al. *Journal of Ethnopharmacology* 120(2008) 233-240; Susa/it E. et al., *Phytomedicine* 18 (2011) 251-258; Perrinjaquet-Moccetti T et al., *Phytotherapy Research* 22, 1239-1242 (2008)). Also, Sedef N El et al. (*Nutrition reviews* 67:11(2009) 632-638) reviewed the cardioprotective activity of olive leaves extracts.

The powerful action of this vegetal against hypertension, thanks to the compounds contained in the leaves of this plant (see the following Table 1, excerpted from Benavente-Garcia et al., *Food Chemistry* 68 (2000) 457-462) is therefore known in the phytotherapic field.

TABLE 1

| Main phenolic groups in OLE | |
|---|---|
| Chemical class | Compound name |
| Oleuropeosides | Oleuropein |
|  | Verbascoside |
| Flavones | Luteolin-7-glucoside |
|  | Apigenin-7-glucoside |
|  | Diosmetin-7-glucoside |
|  | Luteolin |
|  | Diosmetin |
| Flavonols | Rutin |
| Flavan-3-ols | Catechin |
| Substituted phenols | Tyrosol |
|  | Hydroxytyrosol |
|  | Vanillin |
|  | Vanillic acid |
|  | Caffeic acid |

As a matter of fact, compounds such as triterpene (oleanoic acid), flavonoids, secoiridoid bitter glycosides, oleouropein, oleacein, glucosinolates polyphenols and protoanthocyianadins, contained in the leaves of the plants, operate as effective hypotensive and antioxidant substances.

Typically, the extract of dried officinal plants, with special reference to the olive leaf extract, is commonly marketed as a food supplement formulated in capsules, drops, or tablets.

Khemakhem I et al. (Ultrasonics Sonochemistry 34 (2017), 466-473) have demonstrated the advantages of the extraction of olive leaves' bioactive compounds by power ultrasound, in terms of huge amounts of extracted compounds and maintenance of their antioxidant activity. In general, ultra-sounds are advantageous as a method of extractions of active compounds. For instance, CN104922220 discloses a method of preparing a paste of polyphenols from olive oil leaves, wherein the polyphenols are extracted by ultra-sonication of a suspension of dried and powdered olive oil leaves in a bi-phasic aqueous solution that comprises a salt (ammonium sulfate) and an organic solvent (ethanol or methanol).

As a further example, CN104982941 discloses a weight loss nutritional bar comprising, among several other ingredients, a potato extract for inducing satiety, obtained from a mixture of 1 part by mass of potato, 2-10 parts by weight of water, and 0.1-0.5 parts by mass of sodium chloride (corresponding to 0.9-14% of sodium chloride by weight of the potato extract composition); the mixture is grinded and pulverized, then it undergoes two cycles of ultrasonic oscillation, one for 10-20 min at and the other for 5 to 10 min; impurities are eliminated by centrifugation and ultrafiltration, then a dry powder of potato extract is obtained.

However, the prior art does not provide compositions comprising extracts of officinal plants together with common salt, for providing sapidity to food and easy reduction of every day salt intake, further combining the beneficial effects of officinal plants active compounds. Moreover, the prior art does not provide evidence of the possibility to obtain homogeneous and stable dispersions comprising officinal plants extracts and sodium chloride in concentration sufficient to provide the desired sapidity.

The present invention solves the problem of reducing the consumption of salt in the daily diet by providing a salt solution that strongly enhances salty flavours without requiring intake of high amounts of common salt. Moreover, it advantageously combines the benefits deriving from the officinal plants here described with the flavours enhancement, thus counteracting the cardiovascular and renal apparatuses diseases, osteoporosis, water retention and cellulite, caused by salt intake.

Moreover, spray formulations of officinal extracts in salt solutions that contain more than 5% of sodium, which might certainly be more advantageous for a more comfortable and controlled intake of salt, are difficult to obtain because of the poor stability of salt solutions and consequent formation of saline sediments that make administration by spray vaporization impossible, with or without the use of gas.

The salt solution obtained by the process of the invention also solves this problem, being suitable for spray formulations which can be dispensed more easily, even without gas, and with more control on foods.

BRIEF DESCRIPTION OF THE INVENTION

The present invention is directed to a process for the production of a salt solution comprising the steps of:
i. providing a matrix composition (MVH) by mixing: crystals of Halite (a natural source of NaCl), parts of officinal plants and water;
ii. immersing said matrix composition (MVH) in water and leaving it in infusion under stirring;
iii. extract the officinal plants components from the infused MVH by ultra-sonication. Preferably, the ultra-sonication is carried out by applying at least 2 cycles, preferably 5 cycles, of ultrasound to the infused MVH; preferably each cycle is about 30 minutes long and between each cycle an interval of about 2 hours occurs. Preferably, the frequency of ultrasounds is in the range of 25-28 kHz and the power is 2×1500 W.

Preferably, after sonication the infusion is filtered, thus obtaining a salt solution that comprises sodium chloride and officinal plants extracts.

The solution obtained by the process of the invention is homogeneous, having sodium chloride homogeneously and completely dissolved in it, at a concentration of about 30 wt. %. Sodium chloride remains stably in solution during time, without precipitating.

The officinal plants of the MVH composition are preferably selected from the group consisting of: common olive tree, feijoa, garlic, common Hawthorn, basil, capsicum, pepper, rosemary, ginger, common birch, horsetail, green tea, dandelion; more preferably said parts of officinal plants are leaves of common Olive tree; most preferably the leaves are dried ad grinded before being mixed in the MVH composition.

Preferably: said crystals of Halite are present in the MVH in a range of 80-90% mass/mass (w/w); said parts of officinal plants are present in the MVH in a range of 5-15% (w/w); said water is present in the MVH in a range of 0-5% (w/w).

According to a preferred embodiment of the invention, said MVH comprises: about 85% (w/w) of crystals of Halite; about 14% (w/w) of dried leaves of common Olive tree; and about 1% (w/w) of water.

Preferably, the process of the invention further comprises the step of putting the salt solution in a spray dispenser.

The invention is further directed to the salt solution obtained by the process described above.

Preferably, the salt composition of the invention is a condiment, that can be used as flavour enhancer.

Preferably, the salt composition of the invention is a dietary supplement

Preferably, said salt solution is formulated as a spray formulation, being capable of being dispersed by spraying it on food.

Preferably, the salt composition of the invention, more preferably the dietary supplement, is for use in the treatment and/or prevention of a disease caused by salt abuse and/or iodine low dietary intake. Said disease is preferably one or more of cardiovascular disease, hypertension, kidney disease, osteoporosis, water retention and cellulite.

The invention is thus further directed to method of treatment and/or prevention of a disease caused by salt abuse and/or iodine low dietary intake, comprising administering to a subject in need thereof an active dose of the salt composition of the invention. For instance, of up to 80 hits per day of the salt solution in spray formulation, where each hit provides 0.2 mL of solution corresponding to an amount of NaCl less of or equal to 0.06 g.

BRIEF DESCRIPTION OF FIGURES

FIG. 1: chart of solubility of solution A, obtained by the method of the present invention, and of solution B, obtained by mixing 30 wt. % NaCl in water.

DETAILED DESCRIPTION OF THE INVENTION

The present invention refers to a process for producing a salt solution comprising the following steps:

i) creating a matrix composition (MVH), wherein said matrix composition (MVH) comprises a mix of:
   halite crystals;
   parts of officinal plants;
   water;
ii) dipping the matrix composition (MVH) according to item i) in water, preferably purified water, and leaving it in infusion while stirred,
iii) performing an ultrasound extraction of the infusion according to item ii).

In order to prepare the matrix composition (MVH), the halite crystals (HC) are finely smashed and sieved, preferably up to obtaining a granulometry featuring an average diameter equal to 0.60 mm; the parts of officinal plants are sieved and cleaned, preferably by compressed air, washed, and put in a dryer up to eliminating the humidity, and they are subsequently ground.

Then, the halite crystals and the dried and ground parts of officinal plants thus obtained are mixed together while being stirred, to obtain a homogeneous MVH composition (preferably for three hours with self-propelled blades, under a moderate and continuous stirring).

Preferably, said matrix composition (MVH) comprises:
   halite crystals in a range from 80 to 90% by weight of the composition;
   parts of officinal plants in a range from 5 to 15% by weight of the composition;
   water in a range from 0 to 5% by weight of the composition.

Preferably, said officinal parts are dried parts of olive plants.

Even more preferably, said matrix composition (MVH) comprises:
   about 85% of halite crystals (w/w);
   about 14% of dried olive leaves (w/w);
   about 1% of water (w/w).

As already said above, said dried olive leaves comprise one or more components selected from a group consisting of: triterpenes, flavonoids, secoiridoid bitter glycosides, oleacein, glucosinolates polyphenols, protoanthocyanidins.

Preferably the matrix composition (MVH) thus obtained is left in infusion with purified water. Infusion usually proceeds for about 24 hours.

As an example, 300 g of MHV, comprising about 85% (w/w) of halite crystals and about 14% (w/w) of dried olive leaves are infused in pure water to a final volume of 800 mL for 24 hours and then extracted by ultrasounds.

Said ultrasound extraction of the infusion, performed according to item iii) of the process of the present invention, takes place according to usual standard procedures known by those skilled in the art. As a matter of fact, matrix extraction takes place by taking advantage of the mechanical action exerted by the cavitation effect produced by sound waves.

It is known that ultrasounds are emissions of high power sound waves at frequencies typically ranging from 20 kHz to 60 kHz, produced by way of switches which transform electrical energy into mechanical vibrations. The ultrasounds thus produced are transmitted to the vegetal matrix composition (MVH) of the present invention dipped in water (preferably purified water): the aqueous environment is found to be particularly suitable for the extraction process, because the propagation of the ultrasound waves creates microbubbles of air which cause a shock wave, which is referred to as cavitation.

The phenomenon deriving from the ultrasound cavitation thus described results in the breakage of the matrix composition (MVH) and in the disintegration of the cellular structures of the crystals of mineral contained therein. This fosters the coming out of the active ingredients, which solubilize in water. The ultrasound extraction used in the present invention advantageously makes it possible not to use at all the solvents used—and necessary—for a classic extraction of phytotherapic substances.

Preferably, the ultrasound extraction comprises 5 cycles of ultrasounds of 30 minutes each, at a frequency of 25-28 kHz and a power of 2×1500 Watts (W), at time intervals of 2 hours.

The process of the invention can provide a saline solution containing about 25 wt. %, about 28 wt. %, about 30 wt. % NaCl, which also comprises the active components deriving from the officinal plants; the solution thus obtained is then filtered to remove the dry residues.

Preferably, dry residues of infused MHV are pressed and then filtered in order to reduce product losses.

The salt solution deriving from the process of the present invention offers the advantage that the components are homogeneously dispersed in the solution itself; such homogeneous dispersion could not be obtained by simply mixing extracts of officinal herbs and 30 wt. % of NaCl in water, because the individual components, and particularly the saline part, would separate from each other and deposit on the bottom.

In this way, the salt solution according to the present invention enormously enhances the tastes of the dishes because the solution comprises a homogeneous dispersion of sodium which is distributed on the food more effectively while guaranteeing, the contents of sodium being equal and greatly enhancing perception of the salty taste as compared to the conventional systems of use of salt on food.

The present invention not only solves the problem of reducing the use of salt in daily feeding, but it simultaneously offers the benefits deriving from the use of extracts of officinal plants which operate on the problems caused by salt abuse in daily diets.

This invention also avoids the typical problem of humidity accumulation that is experienced with common salt crystals, being common salt crystals highly hygroscopic.

As a matter of fact, advantageously the product of the present invention solves all the above-mentioned problems by combining, on top of it, the possibility of also intaking-along with the salt-phytotherapic active ingredients, either individually or synergistically mixed together, aiming at improving health conditions.

In a preferred embodiment, the salt solution according to the present invention is in a spray formulation, by further putting said saline solution deriving from the above described process in a sprayer. In this way, the saline solution according to the present invention, preferably in a spray formulation, makes it possible to control and modulate the addition of salt to the dishes; typically, the salt solution of the invention is put into a container with a spray dispenser, that dispense 0.2 mL of solution with every hit; in this way at every hit at most about 0.06 g of sodium chloride is constantly dispensed, while providing a salty taste that is much greater (even 5 times more) than the conventional salt dispensed in the classic manner. Furthermore, the spray formulation is more hygienic than typically-used spoons, pinches, salt shakers, etc.

The salt solution of the present invention can therefore be advantageously used as a condiment.

In another embodiment, the present invention refers to a saline food supplement comprising the solution of the present invention to integrate the diet with the phytotherapic active ingredients here described, useful for treating and/or preventing cardiovascular diseases, hypertension, renal pathologies, osteoporosis, water retention, and cellulite.

Preferably, the saline solution of the invention contains about 25 wt. %, 28 wt. %, 30 wt. % NaCl, and extracts of officinal plants parts, preferably olive tree leaves, in a D:E ratio (active compound to extract) of 1:20.

The solution can be administered as spray formulation, at about 20 hits/day (4 mL), corresponding to a maximum of 1.2 g of NaCl and 2.8 g of olive leaves extract.

Preferably, the solution is administered as spray formulation in each meal; at any rate, up to 80 hits per day of the solution do not overcome the WHO's recommended salt day allowance (5 g).

The above described posology is suitable for preventing and/or treating the diseases linked to salt abuse.

A number of explanatory, not limitative examples are illustrated below, aiming at demonstrating the advantageous properties of the present invention.

EXAMPLES

Example 1
Preparing the Matrix Composition MVH

An exemplary way of preparing the matrix composition (MVH) according to the present invention is described hereafter.

The matrix composition (MVH) is a mixture which comprises:

85% of halite crystals by weight of the composition with an average diameter of about 0.06 mm (obtained by smashing and sieving them as described above), mixed with parts (leaves and/or roots and/or other parts of the plant) of an officinal plant (14% by weight) dried and finely smashed, as described above, and water (1% by weight).

Said matrix composition thus obtained is infused in water, then submitted to ultrasound extraction by 5 cycles of 30 minutes each, at a frequency of 25-28 kHz and with a power of 2×1500 W, at intervals of 2 hours, then obtaining, after a final filtering, a highly stable saline solution of the phytotherapic compound, containing about 30% of NaCl by weight of the composition.

Experiments carried out with a salt solution according to the present invention, where the officinal plants are olive leaves, are given below for explanatory purposes, compared to the same experiments carried out with a salt composition prepared according to the state of the art.

Preparing the Samples for Comparing Experiments

As a matter of fact, by:

salt solution A: we mean a saline solution obtained according to the process of the present invention, wherein the parts of officinal plants are olive leaves. At sight, such solution features a light color typical of olives, and is perfectly dissolved.

salt solution B: we mean a reference saline solution formed of water and 30% of NaCl (by weight of the solution) deriving from common table salt.

Materials used 2 laboratory Erlenmeyer flasks made of Pirex glass;
2 magnetic stirrers with cylindrical rod;
1 electronic laboratory balance Tanita KD-200 tested and certified on May 17, 2016;
1 pH and temperature meter Hanna pH211 Microprocessor pH Meter;
1 buffer solution 7.00±0.01/4.01±0.01 Hamilton Duracal Buffer.

Experiments 1000 g of each saline solution were poured into an Erlenmeyer flask made of Pirex glass.

The pH and temperature values were measured with an electrode HI 1131B and a probe HI 7669/2W respectively, by using a laboratory instrument with microprocessor Hanna pH211 Microprocessor pH Meter, properly calibrated before the test with two Hamilton buffer solutions. Solution A was submitted to an intense and continuous stirring for 20 minutes by using the magnetic stirrer with rod, at ambient temperature and pressure.

Comparative Solution B was submitted to an intense and continuous stirring for 20 minutes by means of the magnetic stirrer with rod, at ambient temperature and pressure.

See table 2 hereafter.

TABLE 2

|  | Solution A | Comparative Solution B |
| --- | --- | --- |
| pH | 4.65 | 6.80 |
| Temperature | 20° C. | 20° C. |
| Stirring time (min.) | 20' | 20' |

Evaluating Solubility

Solubility is given by observing the deposits of salt on the bottom of the Erlenmeyer flask after interrupting the stirring induced by the magnetic stirrer (see table 3).

TABLE 3

| Time (min) | Solution A Solubility | Comparative solution (B) Solubility |
| --- | --- | --- |
| 0 | 100% | 100% |
| 3' | 100% | Reduced opalescence |
| 5' | 100% | 50% (Sediment of salt on the bottom of the Erlenmeyer flask) |
| 12' | 100% | 0% (Salt completely separated from water) |

The diagram of FIG. 1 illustrates the difference in solubility of the two saline solutions at ambient temperature.

The diagram clearly shows that the saline solution according to the present invention (A), as early as 10 minutes from interrupting its stirring, maintains solubility, contrary to the reference saline solution (B), which demonstrates a drastic decrement thereof.

Evaluating Stability

The samples of the present invention (A) and of the comparative one (B), prepared as described above, were evaluated for stability.

By stability, we mean the capability of a product of keeping its appearance and its main characteristics, such as taste, density and color, over time. The two samples of saline solution were stored for one month, away from light and heat, in order to simulate their storage in bottles, without the addition of any preservatives.

The following Table 4 shows the results of the tests carried out.

TABLE 4

| Time (days) | Saline solution A Stability | Comparative Saline solution B Stability |
| --- | --- | --- |
| 10 | Homogeneous salt solution, solubility does not change when stirring | Water and salt separated, solubility changes when stirring |
| 20 | Homogeneous salt solution, solubility does not change when stirring | Water and salt separated, solubility changes when stirring |
| 30 | Homogeneous salt solution, solubility does not change when stirring | Water and salt separated, solubility changes when stirring |

Thirty days after, solution A and solution B were put into a bottle with a spray pump for testing their use on meals.

Only saline solution A, i.e. the saline solution according to the present invention, proved to be suitable for being used with the spray proportioning system, because it has remained perfectly fluid and devoid of deposits, and consequently it does not obstruct the cannula of the dip tube of spray dispenser. In the bottle containing solution B, the salt deposited on the bottom obstructed the dispenser.

Evaluating Sapidity (Salty Flavour)

The samples of the present invention (A) were also evaluated for a sensory analysis, in particular for sapidity (salty flavour).

The experiment was carried out at the IBIMET CNR—National Research Council of Italy—Institute in Bologna, Italy, according to the UNI/ISO method 5495:2005 "Methodology-paired comparison test".

Three samples were considered:

Bread with no salt;

Carrots with no salt;

Pasta cooked in water with no salt.

These samples were sprayed with the same quantities of solutions A and B, by using a sprayer capable of dispensing 0.2 ml with each hit.

The samples, thus sprayed, were submitted to a panel of 12 judges trained by IBIMET.

It is worth noting that the samples submitted to the judges were anonymous and identified by 3-digit numbers only.

The concentration of NaCl being equal (30% by weight), the results showed that:

on bread, saline solution A according to the present invention was judged saltier by 11 judges out of 12;

on carrots, saline solution A according to the present invention was judged saltier by 10 judges out of 12;

on pasta, saline solution A according to the present invention was judged saltier by 10 judges out of 12.

The results obtained are summarized in table 5 below.

TABLE 5

| | Bread with no salt (number of judges considering the solution saltier) | Carrots with no salt (number of judges considering the solution saltier) | Pasta cooked in water with no salt (number of judges considering the solution saltier) |
| --- | --- | --- | --- |
| Solution A | 11 | 10 | 10 |
| Comparative Solution B | 1 | 2 | 2 |

The invention claimed is:

1. A process for producing a sodium chloride and officinal plants extracts solution which is suitable for being sprayed, comprising the following steps:

i) provide a matrix composition by mixing:

a) crystals of Halite;

b) parts of officinal plants selected from the group consisting of common olive tree, Feijoa selloviana, garlic, common Hawthorn, basil, *capsicum*, pepper, rosemary, ginger, common birch, horsetail, green tea, and dandelion;

c) water;

ii) immersing the matrix composition of item i) in water and leaving it in an infusion under stirring conditions;

iii) extracting the officinal plants by applying ultrasound to the infusion derived from item ii) to produce a dry residue;

iv) removing the dry residue from the infusion whereby a salt solution is obtained which comprises sodium chloride and the officinal plants extracts.

2. The process of claim 1, wherein said parts of officinal plants comprise leaves of common Olive tree.

3. The process of claim 1, wherein said parts of officinal plants comprise leaves or fruits of Feijoa selloviana.

4. The process of claim 1, wherein the salt solution that is obtained which comprises sodium chloride and the officinal plants extracts comprises about 30% (w/w) sodium chloride.

5. The process of claim 1, wherein said crystals of Halite are present in the matrix composition in a range of 80-90% (w/w); said parts of officinal plants are present in the matrix composition in a range of 5-15% (w/w); said water is present in the matric composition in a range of 0-5% (w/w).

6. The process of claim 1, wherein said matrix composition comprises:

a) about 85% (w/w) of crystals of Halite b) about 14% (w/w) of dried leaves of common Olive tree;

c) about 1% (w/w) of water.

7. The process of claim 1, wherein the salt solution which comprises sodium chloride and the officinal plants extracts also comprises extracts from leaves selected from the group consisting of common Olive tree, wherein said extracts comprise one or more compounds selected from the group consisting of: triterpenes, flavonoids, secoiridoid bitter glycosides, oleacein, glucosinolates polyphenols, and protoanthocyanidins.

8. The process of claim 1, wherein in step iii) 5 cycles of ultrasound are applied to the infused matrix composition of 30 minutes each, with 2 hours of interval between each cycle, and wherein the frequency of ultrasounds is in the range of 25-28 kHz and the power is 2×1500 W.

9. The process of claim 1, further comprising a step of: v) put the salt solution which comprises sodium chloride and the officinal plants extracts salt solution into a spray dispenser.

10. The process of claim 1, wherein the salt solution is a dietary supplement.

11. The process of claim 1, wherein the salt solution is administered to a human in need of iodine.

12. The process of claim 1, wherein the salt solution is added to a food.

* * * * *